US011139059B2

(12) United States Patent
George

(10) Patent No.: US 11,139,059 B2
(45) Date of Patent: Oct. 5, 2021

(54) MEDICAL APPARATUSES CONFIGURED TO RECEIVE SPEECH INSTRUCTIONS AND USE STORED SPEECH RECOGNITION OPERATIONAL DATA

(71) Applicant: Sanofi-Aventis Deutschland GmbH, Frankfurt am Main (DE)

(72) Inventor: Michael George, Frankfurt am Main (DE)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 0 days.

(21) Appl. No.: 16/815,740

(22) Filed: Mar. 11, 2020

(65) Prior Publication Data

US 2020/0211558 A1     Jul. 2, 2020

Related U.S. Application Data

(63) Continuation of application No. 15/791,966, filed on Oct. 24, 2017, now Pat. No. 10,629,198, which is a (Continued)

(30) Foreign Application Priority Data

May 19, 2010   (EP) ..................... 10163305

(51) Int. Cl.
*G16H 20/17*   (2018.01)
*G16H 20/60*   (2018.01)
(Continued)

(52) U.S. Cl.
CPC ............. *G16H 20/17* (2018.01); *G10L 15/22* (2013.01); *G16H 20/60* (2018.01); *G16H 40/63* (2018.01)

(58) Field of Classification Search
USPC ..................................................... 704/1–504
See application file for complete search history.

(56) References Cited

U.S. PATENT DOCUMENTS 5,357,596 A   10/1994   Takebayashi et al.
5,593,390 A    1/1997   Castellano et al.
(Continued)

FOREIGN PATENT DOCUMENTS

DE       10038936 A1      2/2002
JP     2002-091477 A      3/2002
(Continued)

OTHER PUBLICATIONS

International Preliminary Report on Patentability for Application No. PCT/EP2011/058083, dated Nov. 29, 2012.
(Continued)

*Primary Examiner* — Marcus T Riley
(74) *Attorney, Agent, or Firm* — McCarter & English, LLP

(57) ABSTRACT

It is inter alia disclosed to perform at least one of operating an interaction process with a user of the medical apparatus and determining, based on a representation of at least one instruction given by the user, at least one instruction operable by the medical apparatus. Therein, the at least one of the operating and the determining at least partially depends on operational data. It is further disclosed to receive modification information for modifying at least a part of the operational data, wherein the modification information is at least partially determined based on an analysis of a representation of at least one instruction given by the user.

19 Claims, 6 Drawing Sheets

Related U.S. Application Data continuation of application No. 13/697,821, filed as application No. PCT/EP2011/058083 on May 18, 2011, now Pat. No. 9,842,591.

(51) Int. Cl.
*G16H 40/63* (2018.01)
*G10L 15/22* (2006.01)

(56) References Cited

U.S. PATENT DOCUMENTS

| | | | |
|---|---|---|---|
| 6,273,858 B1 | 8/2001 | Fox et al. | |
| 6,366,882 B1 | 4/2002 | Bijl et al. | |
| 6,934,682 B2 | 8/2005 | Woodward | |
| 7,587,469 B2 | 9/2009 | Brown | |
| 8,548,623 B2 | 10/2013 | Poutiatine et al. | |
| 9,135,398 B2 | 9/2015 | Kaib et al. | |
| 9,378,637 B2 | 6/2016 | Kaib et al. | |
| 9,411,800 B2 | 8/2016 | Morin et al. | |
| 9,659,475 B2 | 5/2017 | Kaib et al. | |
| 9,684,767 B2 | 6/2017 | Kaib et al. | |
| 9,842,591 B2* | 12/2017 | George | G10L 15/22 |
| 9,990,829 B2 | 6/2018 | Kaib et al. | |
| 10,269,227 B2 | 4/2019 | Kaib et al. | |
| 10,388,272 B1 | 8/2019 | Thomson et al. | |
| 10,629,198 B2* | 4/2020 | George | G16H 20/60 |
| 2002/0065684 A1 | 5/2002 | Schwalb et al. | |
| 2003/0130853 A1 | 7/2003 | Maire | |
| 2003/0208113 A1 | 11/2003 | Mault et al. | |
| 2005/0171783 A1 | 8/2005 | Suominen | |
| 2005/0283364 A1 | 12/2005 | Longe et al. | |
| 2006/0154642 A1 | 7/2006 | Scannell | |
| 2007/0033026 A1 | 2/2007 | Bartosik et al. | |
| 2007/0168224 A1 | 7/2007 | Letzt | |
| 2007/0276651 A1 | 11/2007 | Bliss et al. | |
| 2008/0077408 A1* | 3/2008 | Wang | G10L 15/22 704/275 |
| 2008/0114594 A1 | 5/2008 | Forbes et al. | |
| 2009/0054754 A1 | 2/2009 | McMahon et al. | |
| 2009/0069867 A1* | 3/2009 | KenKnight | A61B 5/0031 607/60 |
| 2009/0125324 A1 | 5/2009 | Keravich et al. | |
| 2009/0227855 A1 | 9/2009 | Hill et al. | |
| 2011/0040564 A1 | 2/2011 | Laughery et al. | |
| 2011/0202370 A1 | 8/2011 | Green et al. | |
| 2012/0078627 A1 | 3/2012 | Wagner | |
| 2012/0293323 A1 | 11/2012 | Kaib et al. | |
| 2012/0323590 A1 | 12/2012 | Udani | |
| 2013/0138444 A1* | 5/2013 | George | G16H 40/63 704/275 |
| 2013/0268891 A1 | 10/2013 | Finley et al. | |
| 2015/0224330 A1 | 8/2015 | Kaib et al. | |
| 2015/0235541 A1 | 8/2015 | Kaib et al. | |
| 2016/0267765 A1 | 9/2016 | Kaib et al. | |
| 2016/0328529 A1 | 11/2016 | Kaib et al. | |
| 2017/0112671 A1 | 4/2017 | Goldstein | |
| 2017/0278370 A1 | 9/2017 | Kaib et al. | |
| 2018/0047392 A1* | 2/2018 | George | G16H 40/63 |
| 2018/0315286 A1 | 11/2018 | Kaib et al. | |
| 2020/0211558 A1* | 7/2020 | George | G16H 20/17 |

FOREIGN PATENT DOCUMENTS

| | | |
|---|---|---|
| JP | 2005-037662 A | 2/2005 |
| JP | 2010-048890 A | 3/2010 |
| WO | 2002/21510 A1 | 3/2002 |

OTHER PUBLICATIONS

International Search Report for Application No. PCT/EP2011/058083, dated Jun. 30, 2011.

* cited by examiner

MEDICAL APPARATUSES CONFIGURED TO RECEIVE SPEECH INSTRUCTIONS AND USE STORED SPEECH RECOGNITION OPERATIONAL DATA

CROSS REFERENCE TO RELATED APPLICATIONS

The present application is a continuation of U.S. patent application Ser. No. 15/791,966, filed Oct. 24, 2017, which is a continuation of U.S. patent application Ser. No. 13/697,821, filed Feb. 12, 2013, now U.S. Pat. No. 9,842,591, which is a U.S. National Phase application pursuant to 35 U.S.C. § 371 of International Application No. PCT/EP2011/058083 filed May 18, 2011, which claims priority to European Patent Application No. 10163305.5 filed May 19, 2010. The entire contents of these applications are herewith incorporated by reference into the present application.

FIELD OF INVENTION

The present invention relates to the interaction between a user and a medical apparatus and/or to the determination of instructions that may be given by the user in such an interaction.

BACKGROUND

A variety of diseases exists that require regular treatment, which may be supported by use of a medical apparatus.

Examples of such a medical apparatus include an injection device for injecting doses of a medicament. Injection devices are used either by medical personnel or by patients themselves. As an example, type-1 and type-2 diabetes can be treated by patients themselves by injection of insulin doses, for example once or several times per day.

However, in particular older patients and/or patients inexperienced in the use of such a medical apparatus may feel uncomfortable and overstrained when using such a medical apparatus.

To account for this, medical apparatuses with an intuitive usability and interactive guidance have been developed, so that patients feel more confident and comfortable when using such medical apparatuses.

As an example, medical apparatuses with speech recognition capabilities provide intuitive usability and interactive guidance. In this respect, German patent application DE 100 38 936 A1 discloses an injection device for facilitating an adjusting procedure of a dosage of the medicament that is to be injected. This is for instance achieved by providing an audible feedback about the adjusted dosage to the user of the injection device and by recognizing defined speech instructions given by the user.

However, speech recognition of the injection device of DE 100 38 936 A1 is limited to a defined set of recognizable speech instructions. Thus, a user of such an apparatus experiences a low intuitivity due to the limited set of recognizable speech instructions and may suffer from frustration due to low recognition accuracy of speech instructions that deviate from the defined set of recognizable speech instructions.

SUMMARY

It is thus inter alia an object of the present invention to provide apparatuses, a system, methods and computer programs allowing for an improved interaction between a user and a medical apparatus.

According to a first aspect of the present invention, a medical apparatus is disclosed, comprising a processor configured to perform at least one of operating an interaction process with a user of the medical apparatus and determining, based on a respective representation of at least one instruction given by the user, at least one instruction operable by the medical apparatus, wherein the at least one of the operating an interaction process and the determining at least one instruction at least partially depends on operational data; and a communication unit configured to receive modification information for modifying at least a part of the operational data, the modification information at least partially determined based on an analysis of a respective representation of at least one instruction given by a user.

In this first aspect of the present invention, furthermore a method is disclosed, comprising at least one of operating an interaction process with a user of the medical apparatus and determining, based on a respective representation of at least one instruction given by the user, at least one instruction operable by the medical apparatus, wherein the at least one of the operating and the determining at least partially depends on operational data; and receiving modification information for modifying at least a part of the operational data, the modification information at least partially determined based on an analysis of a respective representation of at least one instruction given by a user.

In this first aspect of the present invention, furthermore a computer program is disclosed, comprising program code for performing the method according to the first aspect of the present invention when the computer program is executed on a processor. The computer program may for instance be distributable via a network, such as for instance the Internet. The computer program may for instance be storable or encodable in a computer-readable medium. The computer program may for instance at least partially represent software and/or firmware of the processor.

In this first aspect of the present invention, furthermore a computer-readable medium is disclosed, having a computer program according to the first aspect of the present invention stored thereon. The computer-readable medium may for instance be embodied as an electric, magnetic, electromagnetic, optic or other storage medium, and may either be a removable medium or a medium that is fixedly installed in an apparatus or device. Non-limiting examples of such a computer-readable medium are a Random-Access Memory (RAM) or a Read-Only Memory (ROM). The computer-readable medium may for instance be a tangible medium, for instance a tangible storage medium. A computer-readable medium is understood to be readable by a computer, such as for instance a processor.

In this first aspect of the present invention, furthermore a medical apparatus is disclosed, configured to perform the method according to the first aspect of the present invention.

According to a second aspect of the present invention, an apparatus is disclosed, comprising a processor configured to perform determining, based on an analysis of a respective representation of at least one instruction given by a user of a medical apparatus, the medical apparatus configured to perform at least one of operating an interaction process with a user of the medical apparatus and determining at least one instruction operable by the medical apparatus in dependence on operational data, modification information for modifying at least a part of the operational data; and a communication unit configured to transmit the modification information.

In this second aspect of the present invention, furthermore a method is disclosed, comprising determining, based on an analysis of a respective representation of at least one instruction given by a user of a medical apparatus, the medical apparatus configured to perform at least one of operating an interaction process with a user of the medical apparatus and determining at least one instruction operable by the medical apparatus in dependence on operational data, modification information for modifying at least a part of the operational data; and transmitting the modification information.

In this second aspect of the present invention, furthermore a computer program is disclosed, comprising program code for performing the method according to the second aspect of the present invention when the computer program is executed on a processor. The computer program may for instance be distributable via a network, such as for instance the Internet. The computer program may for instance be storable or encodable in a computer-readable medium. The computer program may for instance at least partially represent software and/or firmware of the processor.

In this second aspect of the present invention, furthermore a computer-readable medium is disclosed, having a computer program according to the second aspect of the present invention stored thereon. The computer-readable medium may for instance be embodied as an electric, magnetic, electro-magnetic, optic or other storage medium, and may either be a removable medium or a medium that is fixedly installed in an apparatus or device. Non-limiting examples of such a computer-readable medium are a Random-Access Memory (RAM) or a Read-Only Memory (ROM). The computer-readable medium may for instance be a tangible medium, for instance a tangible storage medium. A computer-readable medium is understood to be readable by a computer, such as for instance a processor.

In this second aspect of the present invention, furthermore an apparatus is disclosed, configured to perform the method according to the second aspect of the present invention.

According to a third aspect of the present invention, a system is disclosed, comprising a medical apparatus according to the first aspect of the present invention and an apparatus according to the second aspect of the present invention.

In the following, features and embodiments (exhibiting further features) of the present invention will be described, which are understood to equally apply to the apparatuses, methods, computer programs and computer-readable media of the first and second aspect of the present invention, and also to the system according to the third aspect of the present invention. These single features/embodiments are considered to be exemplary and non-limiting, and to be respectively combinable independently from other disclosed features/embodiments of apparatuses, methods, computer programs and computer-readable media of the first and second aspect of the present invention and the system according to the third aspect of the present invention as described above. Nevertheless, these features/embodiments shall also be considered to be disclosed in all possible combinations with each other and with the apparatuses, methods, computer programs and computer-readable media of the first and second aspect of the present invention and the system according to the third aspect of the present invention as described above.

Furthermore, a mentioning that an apparatus according to one of the aspects of the present invention performs (or is configured or arranged to perform) a certain action should be understood to also disclose a corresponding method step of the method according to the respective aspect of the present invention and a corresponding program code of the computer program according to the respective aspect of the present invention.

According to the present invention, the medical apparatus may for instance comprise a processor configured to perform operating an interaction process with a user of the medical apparatus.

Further, the medical apparatus may for instance comprise a processor configured to perform determining, based on a respective representation of at least one instruction given by the user, at least one instruction operable by the medical apparatus.

In an example embodiment, the medical apparatus may for instance comprise a processor configured to perform operating an interaction process with a user of the medical apparatus and determining, based on a respective representation of at least one instruction given by the user (for instance in the interaction process), at least one instruction operable by the medical apparatus.

At least one instruction is given by the user, and a respective representation of the at least one instruction given by the user is used as a basis for determining at least one instruction operable by said medical apparatus. Therein, if only one instruction is given by the user, a representation of this instruction is used, and if two or more instructions are given by the user, representations of these two or more instructions are used, for instance a first representation for a first instruction, a second representation for a second instruction, etc.

The determining, based on a respective representation of at least one instruction given by the user, the at least one instruction operable by the medical apparatus may for instance comprise interpreting a representation of an instruction given by the user and/or mapping, at least partially based on the results of the interpreting, the representation of the instruction given by the user to an instruction operable by the medical apparatus (for instance an instruction from a limited set of instructions that can be operated by the medical apparatus) that causes the medical apparatus to perform a related action. For instance, in the context of injection of medicament doses, the user may speak the instruction "dial 50 units of insulin" and/or "start injection" and, accordingly, the medical apparatus may dial the desired dose of insulin and/or start the injection procedure. In case that the interpreting (or the interpretation, respectively) and/or the mapping fails, the medical apparatus may for instance require the user to give the instruction again or offer action alternatives.

Both, the interpreting and the mapping, is at least partially based on operational data.

The representation of an instruction given by the user may for instance represent the instruction given by the user in a form in which it is sensed and/or processed by means of the medical apparatus, for instance in the form of a signal. Such means may for instance be a sensor configured to capture a signal inputted on a keyboard, a touch-screen device, an adjustment wheel, a button, etc., and/or a means for capturing an acoustical signal (for instance spoken speech, hand clapping, etc.) and/or a means for capturing a visual signal. Due to noise or non-ideal sensor characteristics, the representation of the instruction given by the user may for instance contain additional or less information than the instruction given by the user actually contained. The medical apparatus may for instance comprise more than one of such means/sensors.

It is to be noted that an instruction given by the user is not limited to instructions such as commands, but may for instance be a question, a short (for instance responsive) statement (for instance a single speech instruction) such as yes, no or a number (for instance to indicate to the apparatus to proceed with a respective action).

The operating of an interaction process with a user may for instance comprise determining a reaction that is to be performed by the medical apparatus in response to an action performed by the user. Therefore, the processor configured to perform operating an interaction process may for instance receive information associated with an action performed by the user (for instance a representation of an instruction given by the user, an electronic signal corresponding to such a representation or a change of the status of the medical apparatus) as an input and, at least partially based on this input and on the operational data, the processor then may determine a related reaction.

Accordingly, the interaction process may for instance comprise at least one action performed by the user on the medical apparatus and at least one reaction performed by the medical apparatus in response to this action. Alternatively, the interaction process may for instance comprise at least one action performed by the medical apparatus requiring the user to perform at least one reaction on the medical apparatus in response to this action. However, the interaction process is not limited to one action and one reaction, it may comprise several actions and reactions, wherein one or more actions and/or reactions may be depending on one or more previous actions and/or reactions performed in the flow of the interaction process, so that for instance a verbal/non-verbal dialogue or the like takes place between the user and the medical apparatus. This dialogue may also be partially verbal and partially non-verbal.

An action or a reaction performed by the medical apparatus may for instance be to generate a signal by appropriate means. Such means may for instance be a presentation unit at least comprising one of a visual signal generator (for instance a display device, an indicator light, etc.), an acoustical signal generator (for instance a speaker, a buzzer, etc.), a mechanical signal generator (for instance a vibrator, a Braille display, etc.) or the like.

Parts of the operational data may for instance define how an interaction between the medical apparatus and the user is structured, for instance, what actions and/or instructions are requested and/or expected from the user, and in which sequence. Parts of the operational data may for instance also or alternatively form a basis for the recognition and/or interpretation of instructions given by the user, for instance in the form of databases and/or rules pertaining to and/or defining this recognition/interpretation. The operational data may for instance comprise rules for the determining and/or the operating, such as for instance determining rules, flow rules, and interpretation rules. The operational data may at least partially be stored in a volatile or a non-volatile storage unit that may at least temporarily be comprised in the medical apparatus.

Additionally or alternatively, the storage unit may for instance comprise an operating and/or determining record, which may for instance contain information about at least one previous interaction process (for instance respective representations of actions and reactions of such an interaction process), about respective representations of instructions given by users and respectively determined instructions, medical data (for instance date and dose of injections performed by an injection device), user-specific data, data about device failures and user errors, general data, and/or the like. It may be updated on a regular basis, for instance before, during or after the determining and/or the operating.

The operational data may for instance be modified by instructions that are comprised in the modification information and are operable by the processor of the medical apparatus (or another processor). For instance, instructions for replacing at least a part of the operational data (for instance with data comprised in the modification information), for deleting at least a part of the operational data, for adding new data (for instance comprised in the modification information) to the operational data and/or the like may be comprised in the modification information. Such modifications may also be performed by a user of the medical apparatus, for instance via a user interface. This may require proper authorization of this user.

The analysis based on which the modification information is determined and/or the determining of the modification information is performed by an entity which is not part of the medical apparatus. One or both actions may for instance be performed by the apparatus according to the second aspect of the invention. Therein, the entity may comprise a processor configured to perform the analysis and the determining, or separate processors for these tasks.

The analysis may at least partially comprise determining a respective instruction operable by the medical apparatus based on a respective representation of at least one instruction given by a user of the medical apparatus. To this end, the information on the respective representation of the at least one instruction given by the user has to be provided to the entity that performs the analysis. In the context of speech recognition, for instance a representation of at least one instruction given by the user and not recognized by the medical apparatus (for instance due to unclear pronunciation of the user and/or due to uncommon use of nomenclature) may be analyzed to determine an instruction operable by the medical apparatus that matches the instruction given by the user. The modification information may then be determined accordingly to ensure that the same instruction given by the user is recognized by the medical apparatus in the future.

Furthermore, the analysis may for instance also or alternatively comprise comparing the respective instruction determined by the entity with a respective instruction determined by the medical apparatus in response to the same respective representation of the at least one instruction given by the user, for instance to detect erroneous or non-optimum decisions made by the medical apparatus. To this end, information (e.g. a representative code) on the respective instruction determined by the medical apparatus has to be provided to the entity that performs the analysis. The modification information may then be determined to avoid erroneous or non-optimum decisions of the medical apparatus in the future.

The analysis may for instance also or alternatively comprise comparing a respective representation of at least one user instruction given by a user of the medical apparatus in the flow of an interaction process with another respective representation of at least one user instruction given by the user in the flow of a previous interaction process, or processing respective representations of at least one user instruction given by one or more users of one or more medical apparatuses in several interaction processes (for instance in response to the same question asked to the at least one user in the interaction process). Such information may for instance be analyzed to determine a set of instructions frequently given by the user or users and may be considered when determining modification information, so that for instance the most frequent of all instructions given by the user(s) so far can be recognized by the medical apparatus in the future.

The determining of the modification information may allow the supplementary adaptation of the operating and the determining for instance with respect to a specific user. Thus, the medical apparatus of the first aspect of the present invention is highly flexible and adaptable.

According to an embodiment of the present invention, the at least one instruction is given acoustically by the user and the determining is at least partially based on speech recognition of the respective representation of the at least one instruction given by the user. Similarly, the analysis based on which the modification information is determined may for instance be at least partially based on speech recognition of the respective representation of the at least one instruction given by the user.

Accordingly, the instruction given by the user may for instance be a speech instruction spoken by the user, wherein, in this respect, speech instruction basically relates to any arbitrary speech sounds such as one or more spoken words (i.e. one or more sentences), one or more portions of a spoken word, a single spoken syllable or the like.

The respective representation of the at least one speech instruction given by the user may for instance be captured by an acoustical sensor (e.g. one or more microphones) of the medical apparatus. Initially, this respective representation is thus for instance an electronic signal corresponding to an acoustical representation of the at least one speech instruction, which may for instance be sampled and quantized and subsequently encoded according to a digital audio format, such as for instance the Moving Picture Experts Group (MPEG)-1 Audio Layer 3 (MP3) format or the like. For instance, the acoustical representation comprises the information necessary to play back the sensed speech instruction (e.g. by means of an acoustical signal generator).

The processor configured to perform determining the instruction operable by the medical apparatus based on the respective representation of the at least one speech instruction given by the user may for instance be further configured to perform speech recognition on the representation of the at least one speech instruction given by the user. Therein, the speech recognition may for instance relate to the recognition and/or interpretation of the respective representation of the at least one speech instruction given by the user. This may for instance comprise transcribing the acoustical representation into a text-based representation (for instance speech-to-text conversion), so that a textual representation of the instruction given by the user (or the instruction determined in response to the instruction given by the user) can be visualized, for instance on a display of the medical apparatus. For instance, the text-based representation comprises the textual information (e.g. the words spoken by a user) of the acoustical representation; however, it may for instance not comprise information about the pronunciation/articulation of the words spoken by a user and/or the like.

Furthermore, the processor may for instance be configured to map this text-based representation to an instruction (for instance an instruction from a limited set of instructions) operable by the medical apparatus that causes the medical apparatus to perform an action according to the determined instruction given by the user. The mapping may for instance comprise key-word spotting, contextual analyses based on sensed parameters of the user and/or the medical apparatus, etc. Alternatively, the respective representation of the at least one speech signal given by the user, or parts thereof, may be directly mapped into an instruction operable by the medical apparatus in the process of speech recognition.

According to an embodiment of the present invention, the speech recognition at least partially depends on the operational data, and at least a part of the modification information is determined to improve the speech recognition with respect to the user.

The improvement of the speech recognition may for instance relate to a higher accuracy of the speech recognition (for instance resulting in a lower word error rate) and/or a faster speech recognition (for instance resulting in a smaller real-time factor).

A higher accuracy of the speech recognition may for instance be achieved by modifying the part of the operational data on which the determining of the at least one instruction operable by the medical apparatus is based. This part (which may for instance comprise a set of rules) may for instance consider the specific articulation of specific words of a specific user, a specific vocabulary used by a specific user, specific statistics associated with a specific user (such as probabilities of specific instructions) or the like.

Alternatively or additionally, a higher accuracy of the speech recognition and/or faster speech recognition may for instance be achieved by modifying the part of the operational data (which may for instance comprise a set of rules) that at least partially defines how the interaction process is operated. This part may for instance consider specific statistics associated with the user (such as probabilities of specific instructions) or the like. For instance, several instructions frequently given by the user in response to a single request in the past may be requested from the user in multiple single requests within the flow of the interaction, so that the user can respond by using simple (single) speech instructions.

According to an embodiment of the present invention, the processor may further be configured to recognize a user of the medical apparatus. Modifications of the operational data with respect to the user (for instance user-specific operational data) may then for instance only be considered and/or implemented by the processor if the respective user is recognized. Similarly, the recognition of a user may for instance be necessary to authorize the use of the medical apparatus. The recognition of the user can for instance be performed by speaker recognition.

According to an embodiment of the present invention, the operational data is at least partially associated with at least one of an acoustic model, a language model and a wordbook for the speech recognition. Some or all of the acoustic model, the language model and the wordbook may be user-specific. The acoustic model, the language model and the wordbook may also be specific to a group of users, for example users with the same language, the same or a similar dialect, a similar property of the voice (e.g. high or low pitch, speed of voice, variation in pitch or speed, etc.).

Initially, the speech recognition may for instance at least partially depend on a general acoustic model, a general language model and/or a general wordbook; and these general models may for instance be adapted to a specific user or a group of users by the modification information.

The acoustic model may for instance comprise sound patterns of sequences of words, words, syllabuses and letters; the word book may for instance comprise the recognizable vocabulary of the speech recognition; and the language model may for instance comprise a grammar model or statistical model for determining the most probable sequences of words, words, syllabuses and letters.

According to an embodiment of the present invention, the processor of the medical apparatus is further configured to present the respective representation of the at least one instruction given by the user and the at least one determined instruction. Alternatively, the processor of the medical apparatus may for instance be configured to present at least one of the respective representation of the at least one instruction given by the user and the at least one determined instruction.

In this way, a possibly dangerous misinterpretation and/or an erroneous mapping of the respective representation of the user instruction to an instruction operable by the medical apparatus may be avoided, since the user may respond to the presentation of the respective representation by giving a further instruction (e.g. a corrective feedback). The medical apparatus may thus for instance comprise a button for confirming and/or rejecting the respective representation of the at least one instruction given by the user and/or the at least one determined instruction.

According to an embodiment of the present invention, the modification information is at least partially determined based on an analysis of a respective representation of at least one instruction given by a user in response to the presentation (i.e. the presentation of the respective representation of the at least one instruction given by the user and the at least one determined instruction). The instruction given by the user in response to the presentation provides a feedback that may be considered by determining the modification information (and altering the operational data) accordingly. To this end, information on this feedback may be provided to the entity that performs the analysis.

For instance, an initially erroneously determined instruction operable by the medical apparatus (for instance based on a representation of a speech instruction given by the user) may be corrected by a user in response to the presentation of the determined instruction, so that, in the future, the speech instruction can be mapped to the correct instruction operable by the medical apparatus.

According to an embodiment of the present invention, the operational data is at least partially associated with rules defining at least one of a flow of the interaction process and information provided to the user in the interaction process. These rules may for instance be specific for a user or a class of users, but may alternatively also be general for a large variety of users.

According to an embodiment of the present invention, at least a part of the modification information is determined to modify at least one of the flow of the interaction process and the information provided to the user in the interaction process.

This determined modification information may for instance consider specific statistics associated with the user (such as probabilities/frequencies of specific instructions), highly probable/frequent flows of the interaction process and/or the like. Accordingly, the interaction process may for instance be adapted to a specific user. For instance, if a user has always or at least frequently (for instance always after the first use) skipped certain steps of the interaction, this may be considered in the modification information, and the part of the operational data defining the interaction may be altered accordingly to exclude these frequently skipped steps. The determined modification information may for instance also relate to user-specific data (such as measured parameters of the user, a recommended treatment, medical data, data comprised in the operational data, etc.).

According to an embodiment of the present invention, the interaction process is part of a guidance provided to the user.

The guidance may for instance provide support to the user by providing help, training and/or information (e.g. information regarding exercises, nutrition, diets, administrable drugs and/or the like). This provision may for instance happen in response to a request by the user, or may be at least partially automatically.

According to an embodiment of the present invention, the communication unit of the medical apparatus is further configured to transmit the respective representation of the at least one instruction given by the user based on which the analysis is performed. Additionally, the apparatus according to the second aspect of the present invention may comprise a communication unit configured to transmit the modification information to the medical apparatus.

The receiving and/or the transmitting of the data performed by the medical apparatus and the apparatus according to the second aspect of the present invention may for instance be performed over a wireless and/or a wire-bound link. The wireless link may be based on radio waves, optical waves, sound waves, but also on magnetic or electric fields, to name but a few non-limiting examples.

According to an embodiment of the present invention, the medical apparatus is a medical apparatus configured to administer a medicament. The medical apparatus may for instance be an injection device (such as for instance an injection pen) or an infusion device (such as for instance an infusion pump).

Therein a medicament, also frequently referred to as a "drug", may for instance be understood to be any substance that, when absorbed into the body of a living organism, alters normal bodily function, and/or as any substance used in the treatment, cure, prevention, or diagnosis of disease or used to otherwise enhance physical or mental well-being of a creature. The medicament may for instance be in a solid (e.g. a powder), liquid or gaseous state, or may comprise a mixture of components in solid, liquid and/or gaseous states, such as an aerosol.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N–(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

These and further concepts of the invention will be apparent from and elucidated with reference to the detailed description presented hereinafter.

DETAILED DESCRIPTION

In the following detailed description, exemplary embodiments of the present invention will be described inter alia in the context of a medical apparatus comprising speech recognition means and a server. It is however emphasized that deployment of the present invention in this type of system is of exemplary nature only, since the present invention is equally well applicable in various other contexts.

Figure 1:
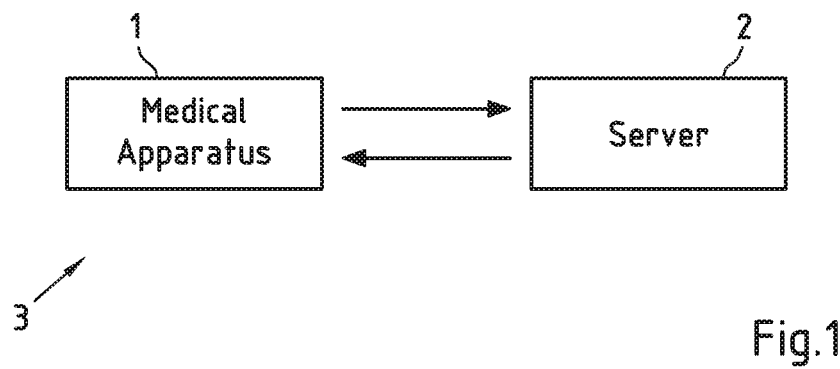
FIG. 1 is a schematic illustration of an embodiment of a system according to the third aspect of the present invention.

FIG. 1 is a schematic illustration of an embodiment of a system according to the third aspect of the present invention. The system comprises at least one medical apparatus 1 and a server 2 that are configured to exchange information with each other.

Figure 2:
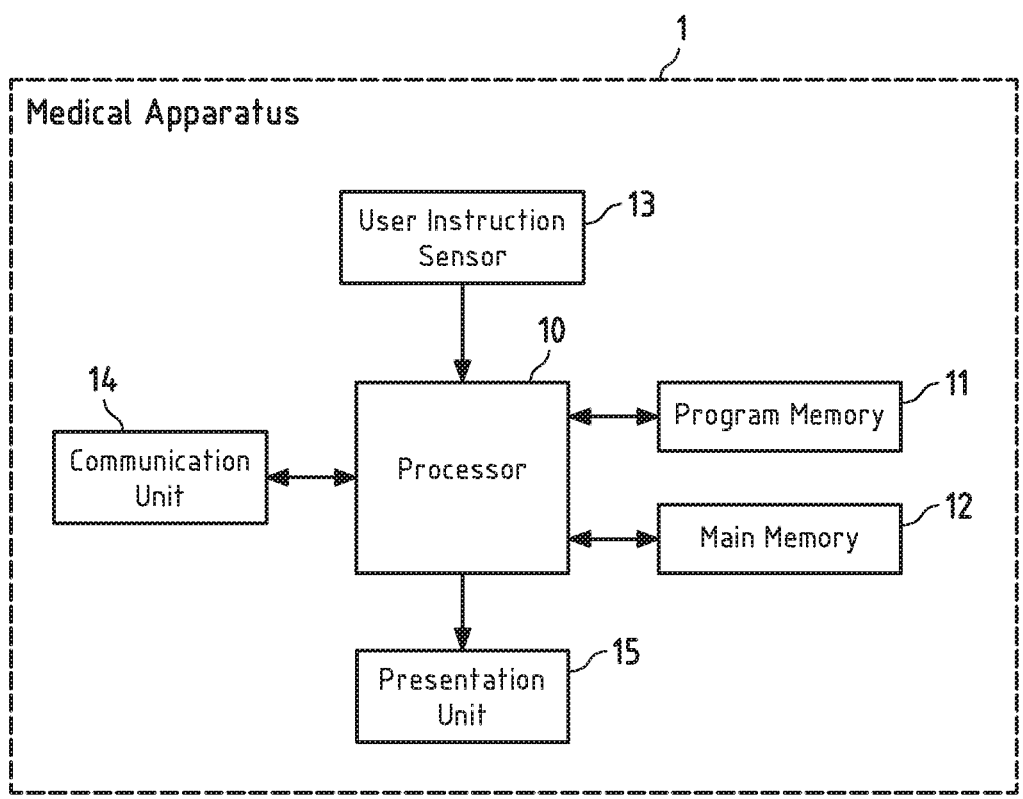
FIG. 2 is a schematic block diagram of an embodiment of a medical apparatus according to the first aspect of the present invention.

FIG. 2 is a schematic block diagram of an embodiment of medical apparatus 1 (see FIG. 1). Medical apparatus 1 comprises a processor 10, which may for instance be a microprocessor, a Digital Signal Processor (DSP), an Application Specific Integrated Circuit (ASIC), a Field Programmable Gate Array (FPGA) or the like. Processor 10 executes program code (e.g. software or firmware) stored in a program memory 11, and uses a main memory 12, for instance to store intermediate results.

Program memory 11 and/or main memory 12 may be used to store at least a part of operational data and/or to keep an operating and/or determining record. Program memory 11 may for instance be a Read-Only Memory (ROM), and main memory 12 may for instance be a volatile or a non-volatile memory such as a Random Access Memory (RAM), a Flash-Memory or the like.

Processor 10 receives input from a user instruction sensor 13, which is for instance a sensor configured to capture a signal inputted on a keyboard, a touch-screen device, an adjustment wheel, a button, and/or the like. The processor 10 may receive further input from a visual sensor (for instance a camera, an acoustical sensor (for instance one or more microphones), and/or from a different/separate/other device.

The user instruction is sensed by user instruction sensor 13. A representation of the user instruction is then forwarded to processor 10.

For instance, user instruction sensor 13 may comprise a microphone configured to sense a speech instruction spoken by a user of medical apparatus 1. The input received by processor 10 may then for instance be an electronic signal corresponding to an acoustical representation of the acoustical signal sensed by the microphone. Alternatively, the electronic signal may for instance correspond to a sampled and quantized and subsequently encoded acoustical representation of the acoustical signal sensed by the microphone. This sampling, quantization and encoding may for instance be performed by an additional processor of user instruction sensor 13. Alternatively, the sampling, quantization and encoding may be performed by processor 10. The sensed acoustical signal comprises the actual speech instruction and for instance background noise or the like.

Optionally (not shown in FIG. 2), processor 10 may receive input from at least one further user instruction sensor (for instance a different type of sensor), at least one user parameter sensor configured to sense a biometric parameter of the user (for instance a blood pressure sensor, a blood glucose meter, or the like) and/or at least one medical apparatus parameter sensor configured to sense a status parameter of medical apparatus 1. For instance, processor 10 may receive input from a microphone and from a sensor configured to capture a signal inputted on a touch-screen device.

Processor 10 further controls a presentation unit 15 comprising at least one of a visual signal generator (for instance a display device, an indicator light, etc.), an acoustical signal generator (for instance a speaker, a buzzer, etc.), a mechanical signal generator (for instance a vibrator, a Braille display, etc.) and the like.

Optionally (not shown), presentation unit 15 may comprise more than one signal generator (for instance signal generator of different types). For instance, presentation unit 15 comprises a display device configured to visually present information, such as a touch-screen device, and a speaker configured to generate a speech signal.

Furthermore, processor 10 controls a communication unit 14, which is for instance configured to transmit and/or receive information to/from one or more other devices in a wireless fashion. Such transmission may for instance be based on radio transmission or optical transmission. Alternatively, communication unit 14 may be configured to transmit and/or receive information to/from another device in a wire-bound fashion, for instance via a cable or fibre connection, both of which may for instance be fixed or releasable. For instance, communication unit 14 may be configured to transmit information (for instance information of the operating and/or determining record) to server 2 and to receive information (for instance modification information) therefrom.

Figure 3:
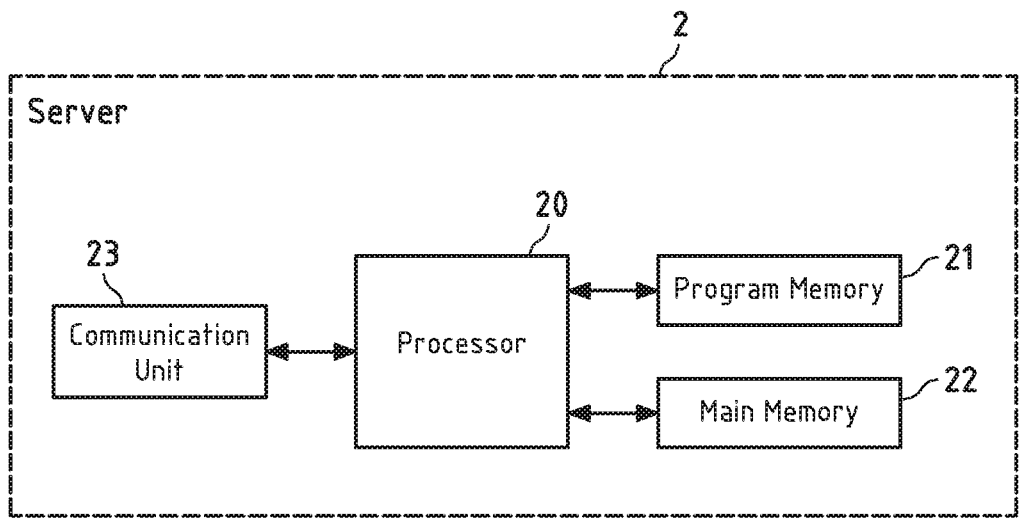
FIG. 3 is a schematic block diagram of an embodiment of an apparatus according to the second aspect of the present invention.

FIG. 3 is a block diagram of an embodiment of server 2 (see FIG. 1). Server 2 comprises a processor 20, which may for instance be embodied as already explained for processor 10 of medical apparatus 1 above. Processor 20 executes program code (e.g. software or firmware) stored in a program memory 21, and uses a main memory 22, for instance to store intermediate results. Program memory 21 and main memory 22 may for instance be embodied as already explained for program memory 11 and main memory 12 of medical apparatus 1 above.

Furthermore, processor 20 controls a communication unit 23, which is for instance configured to transmit and/or receive information to/from one or more other devices in ways already described with reference to communication unit 14 of medical apparatus 1 above. For instance, communication unit 23 may be configured to receive information (for instance information of the operating and/or determining record of medical apparatus 1) from medical apparatus 1 and to transmit information (for instance modification information) thereto. The received information may then for instance be stored in main memory 22.

It is to be noted that the circuitry formed by the components of medical apparatus 1 of FIG. 2 and server 2 of FIG. 3 may be implemented in hardware alone, partially in hardware and in software, or in software only.

FIGS. 4a-4d are flowcharts of embodiments of methods according to the first and second aspect of the present invention.

Figure 4A:
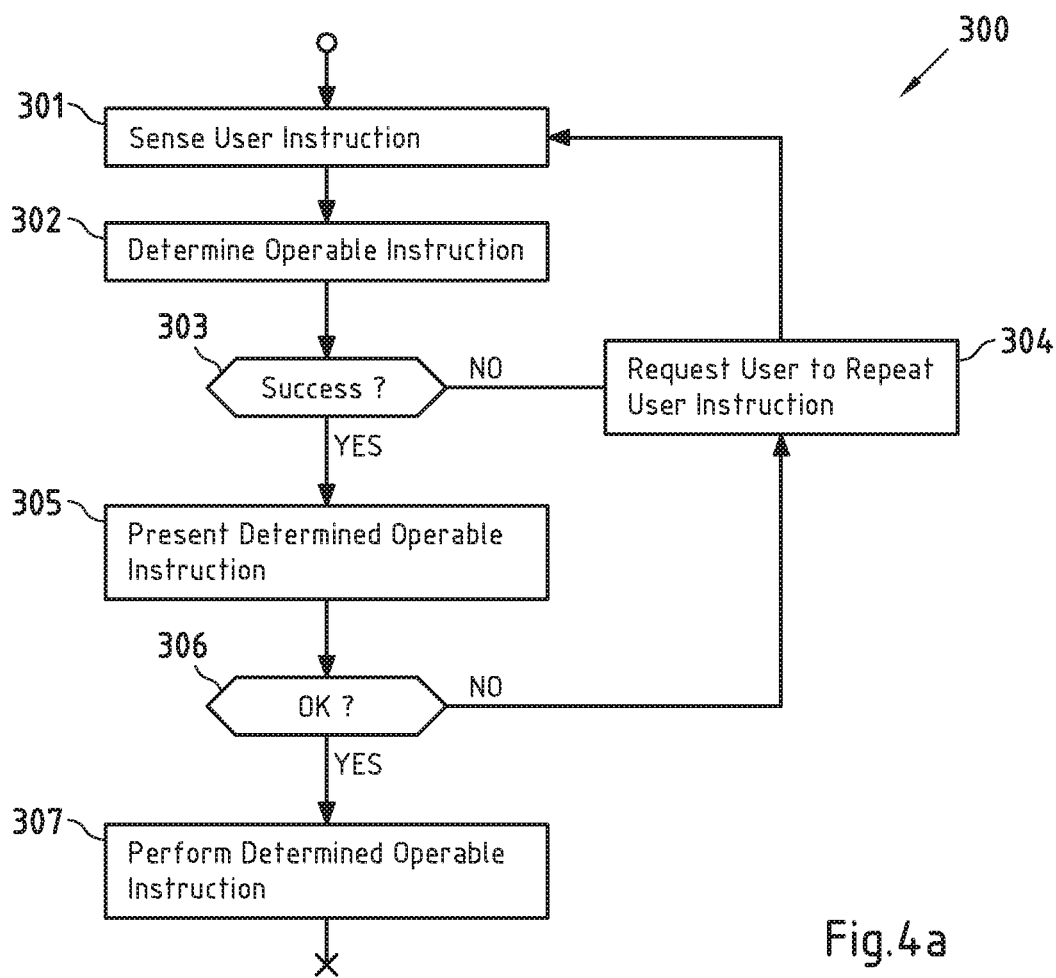
FIG. 4a is a flowchart of an embodiment of a method according to the first aspect of the present invention.

FIG. 4a shows method steps of a flowchart 300 for determining an instruction operable by medical apparatus 1. These method steps may for instance be performed by processor 10 of medical apparatus 1 and may for instance be stored in program memory 11 of medical apparatus 1.

Flowchart 300 starts for instance when the medical apparatus is turned on or is otherwise activated.

In a step 301, an instruction given by a user is sensed, for instance by user instruction sensor 13 of medical apparatus 1 (see FIG. 2). In a step 302, an instruction operable by medical apparatus 1 (i.e. operable instructions) is then determined based on a representation of the instruction given by the user and sensed in step 301.

For instance, the instruction given by the user may be a speech instruction spoken by the user. Accordingly, the determining of the instruction operable by medical apparatus 1 may at least partially be based on speech recognition. Therein, speech recognition may for instance relate to the recognition and/or interpretation of the acoustical representation of the speech instruction spoken by the user. This may for instance comprise transcribing the acoustical representation into a text-based representation.

The recognition and/or interpretation may for instance depend on operational data such as interpretation and/or recognition rules that are for instance at least partially based on an acoustic model and/or a language model and/or a wordbook.

For instance, the recognition and/or interpretation may firstly comprise the identification of sound patterns associated with single words and/or syllabuses in the speech instruction by use of the acoustic model and the wordbook, wherein several word alternatives may be identified. Secondly, based on the language model, the most probable sequence of words is determined. A text-based representation of the speech instruction may represent the sequence of words determined to be most probable.

Furthermore, the text-based representation may be mapped to an instruction (for instance an instruction from a limited set of instructions) operable by medical apparatus 1 that causes medical apparatus 1 to perform a related action. Alternatively, the acoustical representation of the speech signal given by the user, or parts thereof, may be directly mapped to an instruction operable by the medical apparatus in the process of speech recognition. Mapping may for instance be performed by calculating the best matching instruction operable by medical apparatus 1. The mapping may be based on mapping rules comprised in the operational data.

For instance, by comparing the (acoustical and/or text-based) representation with a set of pre-defined representations and calculating the best matching pre-defined representation, the pre-defined representations may be associated with respective instructions operable by the medical apparatus. Therein, the pairs of pre-defined representations and respective instructions are for instance part of the mapping rules.

The calculation may for instance further or alternatively be based on at least one sensed biometric parameter of the user and/or at least one sensed status parameter of medical apparatus 1.

Optionally, determining of the operable instruction may comprise user recognition (for instance speaker recognition). User recognition may for instance be necessary to determine if general operational data or user-specific operational data should be used. Therein, user-specific operational data such as user-specific interpretation rules may for instance provide improved speech recognition, since the speech recognition may for instance be adapted to the specific articulation of a specific user.

In a step 303, the success of step 302 is evaluated.

In the context of the above example, if the calculated best matching instruction has a low-matching score or if the sequence of words determined most probable is rather less probable, the determining may be considered to have failed. This may for instance be the case when the sensed acoustical signal comprises a speech instruction which is disturbed by a high noise level, so that the speech instruction is not recognizable by speech recognition. Equally well, speech recognition may fail in case that a speech instruction does not have a matching instruction operable by the medical apparatus, for instance because the speech instruction uses a rare/unusual vocabulary.

A definition of "low matching score" or "rather less probable" may for instance be given in the mapping and/or interpretation rules that may for instance be comprised in the operational data.

If the determining of step 302 was unsuccessful, in a step 304, the user is requested to repeat his previously given instruction.

For instance, the user may be requested to repeat a non-recognizable speech instruction acoustically. Alternatively, the user may be requested to repeat the non-recognizable speech instruction visually and/or manually.

So, if it is determined that a repetition of a non-recognizable speech instruction will result in another unsuccessful attempt of determining an instruction operable by medical apparatus 1, the user may for instance be requested to input the respective instruction on a touch-screen device, a keyboard or the like, or to spell the instruction letter-by-letter, to give but a few examples. The number of unsuccessful recognitions triggering a change of the way the instruction can be given by the user may be defined by a threshold value (which is 2 in the above example), which may be pre-defined or adaptively determined, for instance based on statistics of the present interaction process and/or one or more previous interaction processes (either with respect to the present user or with respect to a variety of users).

Alternatively, different instruction alternatives may be presented to the user. For instance, the first, second and third best matching instructions operable by the medical apparatus may be presented to the user, who can simply choose one of the alternatives, for instance by speaking a single speech instruction, or by selecting an alternative by touching it on a touch-screen device.

For instance, the user may choose one of the presented instruction alternatives by speaking a single (and thus simply recognizable) speech instruction, e.g. a number associated with the instruction alternative, such as "one", "two" or "three". Alternatively, the user may repeat the speech instruction as requested.

In response to step 304, a user instruction is sensed (step 301), and the method restarts with step 301.

In the case that the determining of the instructions operable by medical apparatus 1 is successful, step 303 is followed by a step 305, in which the determined instruction operable by medical apparatus 1 is (for instance acoustically and/or visually) presented to the user. In a step 306, the user is then requested to confirm the determined instruction.

For instance, the user may confirm the determined instruction by pressing a button, by speaking a single speech instruction, such as "yes" or "ok", or by performing an action on medical apparatus 1 (for instance on a touchscreen thereof). If the user does not confirm the determined instruction, the user is requested to correct the determined instruction and/or to repeat his previously given instruction (step 304). Thereafter, the method restarts with step 301.

However, if the determined operable instruction is confirmed, medical apparatus 1 is caused to perform the operable instruction in a step 307.

Optionally, information related to the steps of flowchart 300, such as the representation of the instruction given by the user (step 301), the determined instruction operable by medical apparatus 1 (302), the representation of the repeated instruction given by the user (steps 304, 301), sensed biometric parameters and/or sensed medical apparatus parameters, are stored in the operating and/or determining record.

For instance, the acoustical and/or text-based representation of a speech instruction spoken by the user, the respectively determined instruction, and the respective corrected determined instruction (if correction was necessary, see steps 306, 304, 301) may be stored in the operating and/or determining record.

Figure 4B:
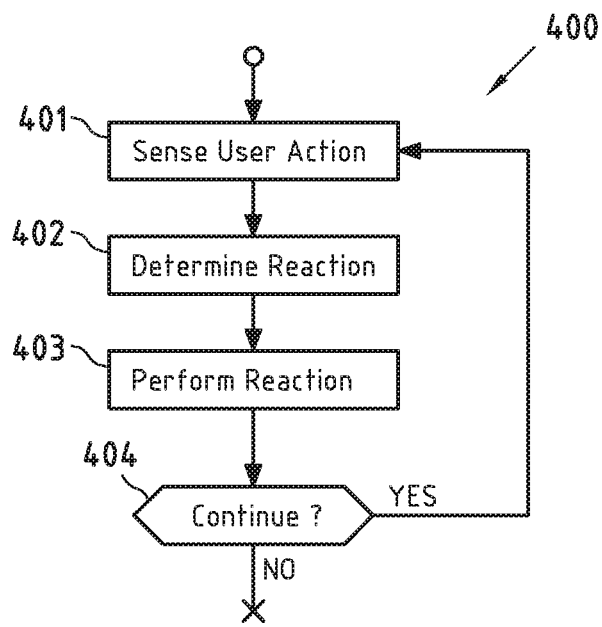
FIG. 4b is a flowchart of a further embodiment of a method according to the first aspect of the present invention.

FIG. 4b shows method steps of a flowchart 400 for operating an interaction process. These method steps may for instance be performed by processor 10 of medical apparatus 1 and may for instance be stored in program memory 11 of medical apparatus 1.

In a step 401, an action performed by a user of medical apparatus 1 is sensed. Such an action may for instance be an instruction given by the user, or it may for instance be an action causing a change of the status of medical apparatus 1, such as a turning medical apparatus 1 on.

In a step 402, a reaction that is to be performed by medical apparatus 1 in response to the action sensed in step 401 is determined, at least partially based on information associated with the sensed action.

For instance, if the sensed action is a speech instruction spoken by the user, the determining of the reaction may at least partially be based on speech recognition. Therein, speech recognition may for instance relate to the recognition and/or interpretation of the respective acoustical representation of the speech instruction spoken by the user, as described above.

Furthermore, a representation of the recognized speech instruction (for instance a text-based representation) may then be mapped to a reaction that is performable by medical apparatus 1. Alternatively, the acoustical representation of the speech instruction, or parts thereof, may be directly mapped to a reaction that is performable by medical apparatus 1.

Determining of the reaction may for instance at least partially be based on calculating the best matching reaction performable by medical apparatus 1. The calculation may be based on flow rules comprised in the operational data.

In the context of a spoken speech instruction, for instance an acoustical and/or text-based representation of the speech instruction is compared with a set of pre-defined representations and the best matching pre-defined representation is calculated. The pre-defined representations may be associated with respective reactions performable by the medical apparatus; and the pairs of pre-defined representations and respective reactions are for instance part of the flow rules.

The calculation may for instance further or alternatively be based on at least one sensed biometric parameter of the user, at least one sensed status parameter of medical apparatus 1 and/or at least one previously sensed action and/or reaction.

The flow rules may for instance define how an interaction between the medical apparatus and the user is structured, for instance, what actions and/or instructions are requested and/or expected from the user, and in which sequence.

A determined reaction that is performable by medical apparatus 1 may for instance be the presentation of information (for instance by generating a speech signal), or the change of the status of medical apparatus 1, to name but a few examples.

In a step 403, the medical apparatus is caused to perform the determined reaction; and in a step 404, it is determined whether the interaction process is to be continued.

Optionally, information related to the steps of flowchart 400, such as a representation of the flow of the interaction process and/or representations of the actions performed by the user in the course of the flow (step 401), the determined actions performable by medical apparatus 1 (step 402), sensed biometric parameters and/or sensed medical apparatus parameters, are stored in the operating and/or determining record.

For instance, if an interaction process, such as a dialog for preparing the injection of a medicament (such as for instance insulin) by medical apparatus 1, requires the user to perform different actions, the user is sequentially requested to do so. In this case, the user may firstly be requested to change the needle or needle device of the injection device. As soon as a needle-change (i.e. a status change) is sensed, the user may be asked to perform a priming shot (and/or a safety shot and/or a safety test). After the priming shot the user is requested to give an instruction (for instance a speech instruction) with respect to the desired dose of insulin that is to be ejected. Thereafter, the user is requested to confirm the accordingly determined dose (which may for instance be determined at least partially by speech recognition). When a confirmation is sensed, the determined dose is ejected by medical apparatus 1. Thus, several reactions and actions depending on the previous reactions and actions are part of this exemplary interaction process and, thus, the method steps 401-404 are repeated several times.

Figure 4C:
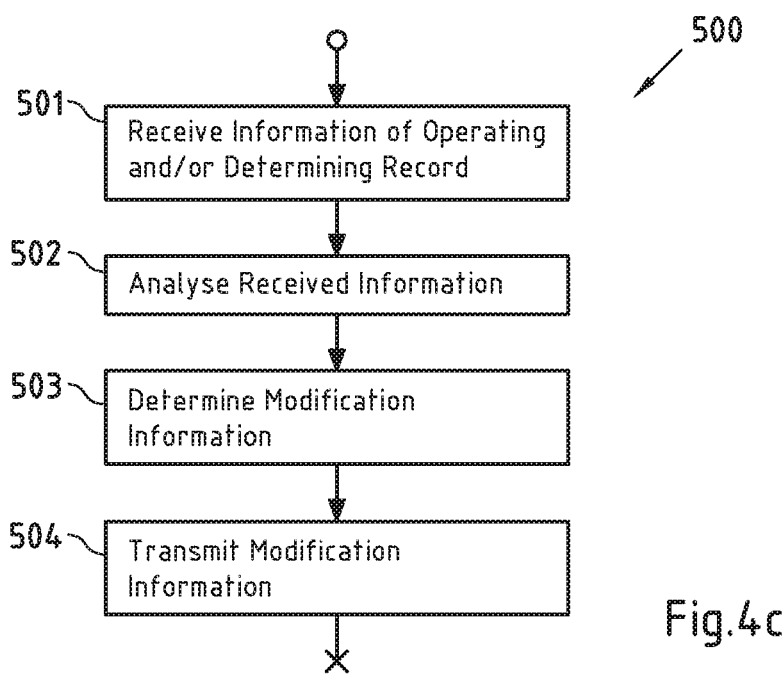
FIG. 4c is a flowchart of an embodiment of a method according to the second aspect of the present invention.

FIG. 4c shows a flowchart 500 with method steps that are for instance performed by processor 20 of server 2 (see FIG. 3) and may for instance be stored in program memory 21 of server 2.

In a step 501, information of an operating and/or determining record is received, for instance from medical apparatus 1.

The received information comprises at least one representation of at least one instruction given by a user of medical apparatus 1. For instance, an acoustical representation of a speech instruction spoken by the user (see step 301 of FIG. 4a) and/or a respective text-based representation (see step 302 of FIG. 4a) may be received.

Optionally, the received information may comprise further information about at least one previous interaction process (for instance respective representations of actions (see step 401 of FIG. 4b) and reactions (see step 402 of FIG. 4b) of such an interaction process), further respective representations of instructions given by at least one user and respectively determined instructions, medical data (for instance date and dose of injections performed by an injection device), user-specific data, data about device failures and user errors, general data, and/or the like.

In a step 502, the received information is analyzed, and in a step 503, modification information is determined at least partially based on the analysis of the information.

In the context of at least partially speech-based control of medical apparatus 1, for instance a representation of at least one speech instruction spoken by the user and not recognized by medical apparatus 1 (for instance due to unclear pronunciation of the user and/or due to uncommon use of nomenclature) may be analyzed to determine an instruction operable by the medical apparatus that matches the instruction given by the user. The modification information may then be determined accordingly to ensure that the same instruction given by the user is recognized by the medical apparatus in the future.

Furthermore, the analysis may for instance also or alternatively comprise comparing the instruction determined by server 2 with an instruction determined by the medical apparatus 1 in response to the same representation of an instruction given by the user, for instance to detect erroneous or non-optimum decisions made by medical apparatus 1. To this end, information (e.g. a representative code) on the respective instruction determined by medical apparatus 1 has to be provided to server 2 that performs the analysis. The modification information may then be determined to avoid erroneous or non-optimum decisions of the medical apparatus 1 in the future.

The analysis may for instance further or alternatively comprise comparing a representation of an instruction given by a user of medical apparatus 1 in the flow of an interaction process with another representation of an instruction given by the user in the flow of a previous interaction process, or processing representations of an instruction given by one or more users of one or more medical apparatuses in several interaction processes (for instance in response to the same question asked to the at least one user in the interaction process). Such information may for instance be analyzed to determine a set of instructions frequently given by the user or users of the medical apparatus 1 (or by users of identical or at least functionally similar medical apparatuses) and may be considered when determining modification information, so that for instance the most frequent of all instructions given by the user(s) so far can be recognized by the medical apparatus 1 in the future. Alternatively, the most frequent of all instructions may be presented as instruction alternatives to the user, so that the user may for instance respond with a single (and thus simply recognizable) speech instruction, such as "one", "two", or "three".

The modification information may comprise information for modifying the operational data generally (i.e. for all users) and/or for modifying the operational data for a specific user (for instance to adapt the speech recognition to a specific articulation that is characteristic for the user) or for a specific group of users.

The determining of the modification information may further be based on a server-side copy of the operational data stored in medical apparatus 1, so that the determined modification information for instance comprises only modified parts of the operational data. Alternatively, the information received from medical apparatus 1 may comprise the entire operational data, and/or the transmitted modification information comprises the entire modified operational data, although only parts thereof may have been actually modified.

Figure 4D:
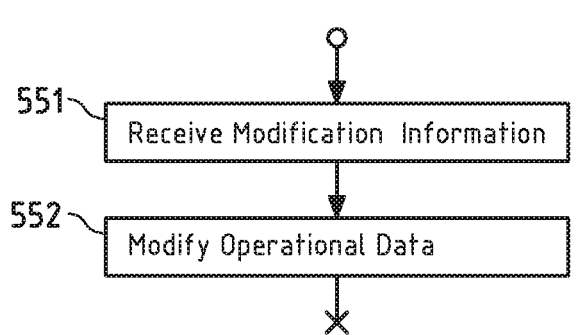
FIG. 4d is a flowchart of further method steps performed in an embodiment of a method according to the first aspect of the present invention.

FIG. 4d shows a flowchart 550 with method steps that are for instance performed by processor 10 of medical apparatus 1 (see FIG. 1) and may for instance be stored in program memory 11 of medical apparatus 1.

In a step 551, modification information is received, for instance from server 2.

As described above, the modification information may comprise information for modifying the operational data generally (i.e. for all users) and/or for modifying the operational data for a specific user (for instance to adapt the speech recognition to a specific articulation that is characteristic for the user).

In a step 552, the operational data is then modified based on the received modification information.

Therein, the modification information may comprise instructions that are for instance operable by processor 10 or by another processing unit (for instance by a processor comprised in a modification unit) for modifying the operational data. These instructions are for instance for replacing at least a part of the operational data (for instance with data comprised in the modification information), for deleting at least a part of the operational data, and/or for adding new data (for instance comprised in the modification information) to the operational data.

Optionally, the received modification information are analyzed, so that it may for instance be determined whether the modification of the operational data is performed for all users, or for a specific group of users, or for a specific user. For instance, the operational data may comprise general interpretation and mapping rules for all users and supplementary and/or alternative interpretation and mapping rules for at least one specific user or at least one group of specific users. However, if medical apparatus 1 is only used by one specific user, only interpretation and mapping rules for the specific user may be maintained when modification information is received.

Figure 5:
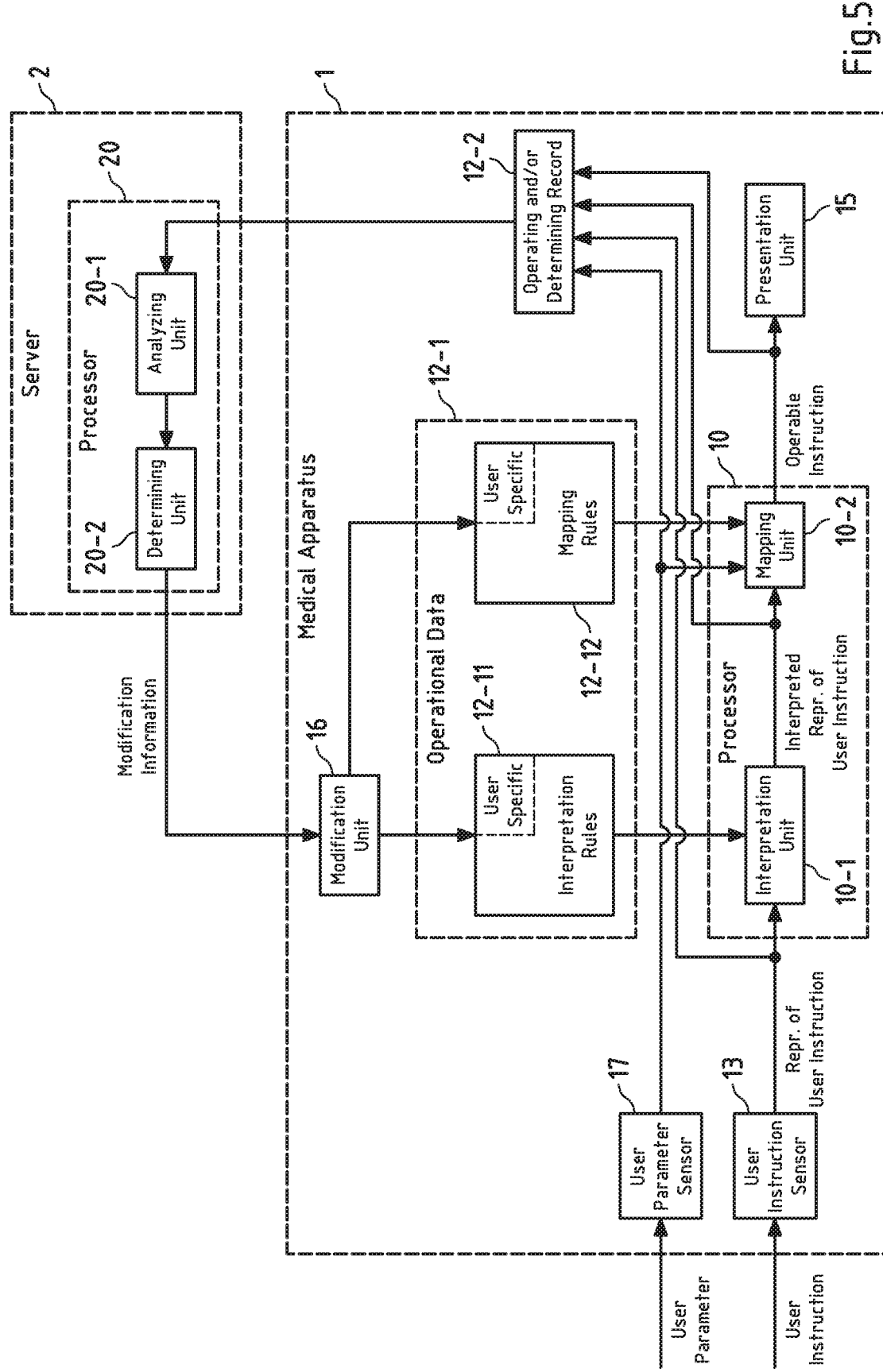
FIG. 5 is a schematic block diagram that illustrates an information flow and a processing according to an embodiment of the present invention

FIG. 5 is a schematic block diagram that illustrates an embodiment of an information flow and processing in system 3 (see FIG. 1) of the present invention. Therein, components that have the same function as components already shown in FIGS. 2 and 3 have been assigned the same reference numerals.

An instruction given by a user (for instance a speech instruction) is sensed by user instruction sensor 13 comprised in medical apparatus 1. User instruction sensor 13 forwards an electronic signal corresponding to a representation of the instruction (for instance an acoustical representation of the speech instruction) to processor 10.

Processor 10 comprises an interpretation unit 10-1 and a mapping unit 10-2 for performing the determining of an instruction operable by medical apparatus 1 based on the forwarded representation, on operational data 12-1 and optionally on one or more user parameters sensed by user parameter sensor 17. In particular, determining the instruction operable by medical apparatus 1 may for instance be performed as described above.

Interpretation unit 10-1 performs recognition and/or interpretation on the forwarded representation according to interpretation rules 12-11 (for instance according to general and/or user specific interpretation rules) comprised in operational data 12-1, and outputs an interpreted representation of the user instruction (for instance a text-based representation of the speech instruction).

This interpreted representation is then used by mapping unit 10-2 to map the representation of the instruction given by the user with the best-matching instruction operable by medical apparatus 1. The mapping is performed according to mapping rules 12-12 (for instance general and/or user specific mapping rules) comprised in operational data 12-1.

The determined operable instruction is then communicated to presentation unit 15 configured to present the determined instruction to the user (for instance by generating a corresponding speech signal). Optionally (not shown), processor 10 may further or alternatively cause medical apparatus 1 to perform a related action.

Additionally, the representation of the user instruction, the interpreted representation of the user instruction, the determined operable instruction and the optionally sensed user parameter are recorded in operating and/or determining record 12-2.

Both, operational data 12-1 and operating and/or determining record 12-2 may for instance be comprised in main memory 12 shown in FIG. 2.

This information of operating and/or determining record 12-2 is then communicated to server 2.

Processor 20 of server 2 comprises an analyzing unit 20-1 for analyzing the communicated information of determining and/or operating record 12-2; and it further comprises a determining unit 20-2 configured to perform determining modification information at least partially based on the analysis. Furthermore, the determining modification information may further or alternatively be based on the operational data, a server-side copy of the operational data, previously communicated information of operating and/or determining record 12-2 and/or information of operating and/or determining record communicated from further medical apparatuses. In particular, the analysis of the communicated information and the determining of the modification information may be performed as described above.

The determined modification information is then communicated to modification unit 16 of medical apparatus 1, which is for instance comprised in processor 10, or which is a separate processing unit. Modification unit 16 is configured to modify operational data 12-1, such as interpretation rules 12-11 and mapping rules 12-12 according to instructions comprised in the determined modification information.

Optionally, modification unit 16 may for instance be further configured to modify the operational data in an interaction process or upon one or more instructions given by a user, such as a specific user. The user then may for instance use a user interface of medical apparatus 1 for modifying the operational data 12-1.

Figure 6:
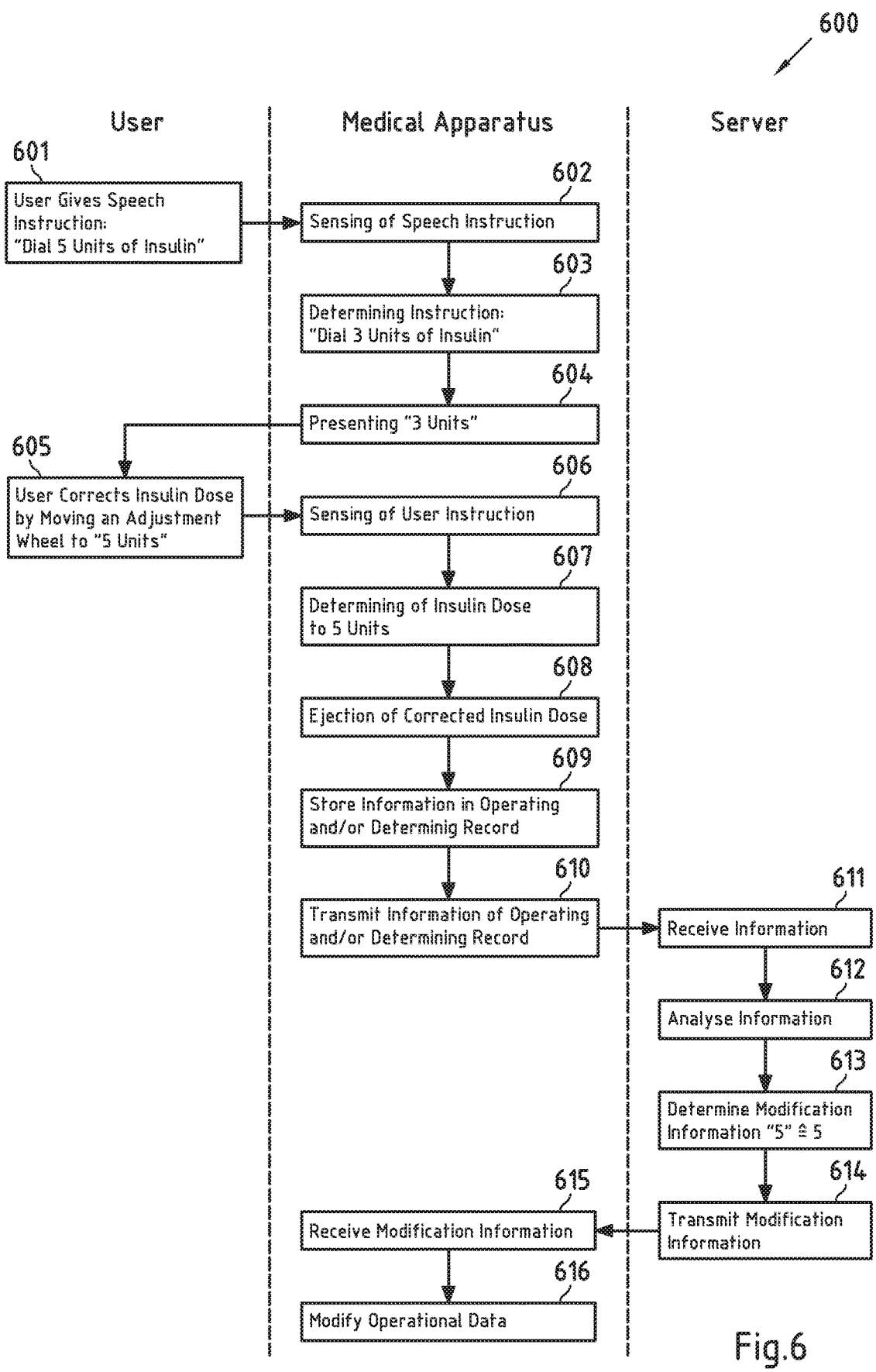
FIG. 6 is a flowchart that illustrates an information flow and a processing according to a further embodiment of the present invention.

FIG. 6 is a flowchart 600 that illustrates an information flow and processing according to an embodiment of the present invention.

In a step 601, the user gives the speech instruction "dial 5 units of insulin".

This speech instruction is sensed by medical apparatus 1 in a step 602. However, in a step 603, the related instruction operable by the medical apparatus is wrongly determined to "dial 3 units of insulin", for instance due to unclear pronunciation of the user instruction, in particular of the word "5".

In a step 604, the wrongly determined instruction is then presented to the user, who accordingly corrects the wrongly determined instruction, for instance by moving an adjustment wheel to a position corresponding to the instruction "dial 5 units of insulin".

In a step 606, the position of the adjustment wheel is then sensed by medical apparatus 1; and in a step 607 the instruction operable by the medical apparatus is correctly determined to "dial 5 units of insulin".

Optionally, the correctly determined instruction may then be presented to the user, who may confirm the correctly determined instruction.

In a step 608, the correctly determined 5 units of insulin are then ejected by medical apparatus 1.

In a step 609, the representation of the speech instruction sensed in step 602 and the in step 603 wrongly determined instruction and/or the representation of the instruction sensed in step 606 and/or the instruction determined correctly in step 607 may be stored in an operating and/or determining record. This information may then be transmitted (step 610) by medical apparatus 1 and received by server 2 (step 611).

In a step 612, the received information may be analyzed; and in a step 613 modification information may be determined. In this case, the modification information may for instance comprise information, so that the instruction wrongly determined in step 603 will be correctly determined in the future.

This modification information is transmitted from server 2 (step 614) and received by medical apparatus 1 (step 615).

In a step 615, the operational data is then modified accordingly.

For instance, the user may have a specific articulation of the number "5", so that the general acoustic model or a user specific acoustic model that may initially be comprised in the interpretation rules may be modified according to information comprised in the received modification information. Alternatively, the speech instruction (sensed in step 602) may comprise a word, which is not comprised in the word-book comprised in the interpretation rules, so that the word-book may be updated according to the received information.

Figure 7:
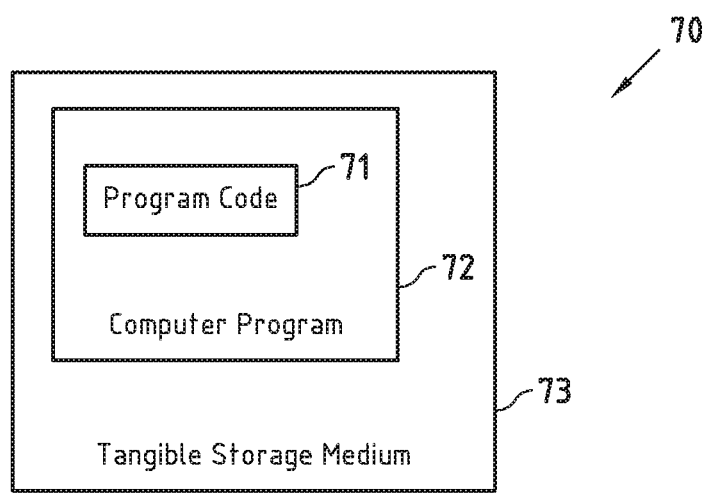
FIG. 7 is a schematic illustration of a tangible storage medium according to an embodiment of the present invention.

FIG. 7 is a schematic illustration of an embodiment of a tangible storage medium 73 that comprises a computer program 72 with program code 73 according to an embodiment of the present invention. This program code may for instance be executed by processors contained in medical apparatus 1, for instance processor 10, but also processor 20 contained in server 2. For instance, storage medium 73 may represent program memory 11 of medical apparatus 1 or program memory 21 of server 2. Storage medium 73 may be a fixed memory, or a removable memory, such as for instance a memory stick or card. Tangible storage medium 73 is a non-transitory storage medium.

It should also be understood that the sequence of method steps in the flowcharts presented above is not mandatory, also alternative sequences may be possible. All functional blocks of apparatuses shall also be understood as a disclosure of a corresponding method step, and similarly, each method step shall be considered as a disclosure of a corresponding functional unit of an apparatus. It is well understood that the method steps and functional components can be implemented in various ways either in hardware only, or in software only, or in a combination of hard- and software.

What is claimed is:

1. An injection or infusion device configured to administer a medicament via a needle, the injection or infusion device comprising:
a processor;

one or more microphones configured to receive a speech instruction spoken by a user; and a non-transitory computer readable storage medium comprising operational data including one or more interpretation rules, and instructions that, when executed by the processor, cause the processor to control the injection or infusion device to perform operations comprising:

receiving via the one or more microphones a speech instruction spoken by a user of the injection or infusion device;

performing speech recognition on the speech instruction spoken by the user of the injection or infusion device to determine an interpreted representation of the speech instruction using, at least in part, the one or more interpretation rules; and determining a dose of the medicament to be administered by the injection or infusion device based upon the speech recognition performed on the speech instruction spoken by the user of the injection or infusion device.

2. The injection or infusion device of claim 1, wherein the interpreted representation is a text-based representation.

3. The injection or infusion device of claim 1, wherein the one or more interpretation rules comprise one or more user-specific interpretation rules associated with one or more specific users, and wherein the instructions, when executed by the processor, cause the processor to control the injection or infusion device to perform a further operation comprising:

recognizing whether the user of the injection or infusion device is a specific user associated with the one or more user-specific interpretation rules; wherein, where the user of the injection or infusion device is a specific user associated with the one or more user-specific interpretation rules, the performing speech recognition uses, at least in part, the one or more user-specific interpretation rules associated with the specific user.

4. The injection or infusion device of claim 3, wherein the one or more user-specific interpretation rules comprise an articulation of words by the user of the injection or infusion device.

5. The injection or infusion device of claim 3, wherein the instructions, when executed by the processor, cause the processor to control the injection or infusion device to perform a further operation comprising:
authorizing use of the injection or infusion device based on the recognizing of the user of the injection or infusion device to be a specific user associated with the one or more user-specific interpretation rules.

6. The injection or infusion device of claim 3, wherein the instructions, when executed by the processor, cause the processor to control the injection or infusion device to perform a further operation comprising modifying the one or more user-specific interpretation rules with respect to the user of the injection or infusion device only if the user of the injection or infusion device is recognized and authorized.

7. The injection or infusion device of claim 3, wherein the instructions, when executed by the processor, cause the processor to control the injection or infusion device to perform a further operation comprising authorizing use of the injection or infusion device only if the user of the injection or infusion device is recognized to be a specific user associated with the one or more user-specific interpretation rules that is authorized.

8. The injection or infusion device of claim 3, wherein the one or more interpretation rules further comprise one or more general interpretation rules; and wherein the instructions, when executed by the processor, cause the processor to control the injection or infusion device to perform a further operation comprising:

based on whether the user of the injection or infusion device is recognized to be a specific user associated with the one or more user-specific interpretation rules, determining whether the one or more general interpretation rules, the one or more user-specific interpretation rules, or both should be used for performing the speech recognition.

9. The injection or infusion device of claim 1, wherein the operational data further includes one or more mapping rules, and wherein the instructions, when executed by the processor, cause the processor to control the injection or infusion device to perform a further operation comprising:

mapping the interpreted representation of the speech instruction to an operation performable by the injection or infusion device, using, at least in part, the one or more mapping rules.

10. The injection or infusion device of claim 9, wherein the mapping comprises performing at least one of key-word spotting and contextual analyses.

11. The injection or infusion device of claim 9, wherein the one or more mapping rules comprise a plurality of pairs of pre-defined representations and respective instructions.

12. The injection or infusion device of claim 9, wherein the one or more mapping rules comprise one or more user-specific mapping rules associated with one or more specific users, and wherein the instructions, when executed by the processor, cause the processor to control the injection or infusion device to perform a further operation comprising:

recognizing whether the user of the injection or infusion device is a specific user associated with the one or more user-specific mapping rules; wherein, where the user of the injection or infusion device is a specific user associated with the one or more user-specific interpretation rules, the mapping uses, at least in part, the one or more user-specific mapping rules associated with the specific user.

13. The injection or infusion device of claim 12, wherein the one or more user-specific mapping rules comprise at least one of vocabulary used by the one or more specific users, and statistics associated with instructions of the one or more specific users.

14. The injection or infusion device of claim 12, wherein the one or more interpretation rules further comprise one or more general mapping rules; and wherein the instructions, when executed by the processor, cause the processor to control the injection or infusion device to perform a further operation comprising:

based on whether the user of the injection or infusion device is recognized to be a specific user associated with the one or more user-specific mapping rules, determining whether the one or more general mapping rules, the one or more user-specific mapping rules, or both should be used for performing the speech recognition.

15. The injection or infusion device of claim 1, wherein the injection or diffusion device is an injection pen or an infusion pump.

16. The injection or infusion device of claim 1, wherein the instructions, when executed by the processor, cause the processor to control the injection or infusion device to perform a further operation comprising: displaying a textual representation of the speech instruction spoken by the user of the injection or infusion device on a display of the injection or infusion device.

17. The injection or infusion device of claim 1, wherein the instructions, when executed by the processor, cause the processor to control the injection or infusion device to perform further operations comprising:
    transcribing the speech instruction spoken by the user of the injection or infusion device into a text-based representation; and
    presenting the text-based representation of the speech instruction spoken by the user of the injection or infusion device via a presentation unit of the injection or infusion device.

18. A tangible, non-transitory, computer-readable medium comprising instructions for operating an injection or infusion device configured to administer a medicament via a needle, the injection or infusion device including a processor and one or more microphones, the instructions, when executed on the processor, causing the injection or infusion device to perform operations comprising:
    receiving, via the one or more microphones, a speech instruction spoken by a user of the injection or infusion device;
    performing speech recognition on the speech instruction spoken by the user of the injection or infusion device to determine an interpreted representation of the speech instruction using, at least in part, one or more interpretation rules stored within the injection or infusion device; and
    determining a dose of the medicament to be administered by the injection or infusion device based upon the speech recognition performed on the speech instruction spoken by the user of the injection or infusion device.

19. A method, performed by one or more processors, for operating an injection or infusion device configured to administer a medicament via a needle, the method comprising:
    receiving an interpreted representation of a speech instruction spoken by a user of the injection or infusion device, wherein the interpreted representation is determined by performing speech recognition using, at least in part, one or more interpretation rules;
    mapping the interpreted representation of the speech instruction to an operation performable by the injection or infusion device, using, at least in part, one or more mapping rules; and
    determining a dose of the medicament to be administered by the injection or infusion device based upon the speech recognition performed on the speech instruction spoken by the user of the injection or infusion device.

* * * * *